United States Patent
Cohen

(10) Patent No.: US 10,702,590 B2
(45) Date of Patent: Jul. 7, 2020

(54) COMPOSITIONS AND METHODS FOR TREATING THYROID DISEASE

(71) Applicant: Script Essentials, LLC, Broomfield, CO (US)

(72) Inventor: Suzy Cohen, Broomfield, CO (US)

(73) Assignee: Script Essentials, LLC, Broomfield, CO (US)

( * ) Notice: Subject to any disclaimer, the term of this patent is extended or adjusted under 35 U.S.C. 154(b) by 399 days.

(21) Appl. No.: 15/478,505

(22) Filed: Apr. 4, 2017

(65) Prior Publication Data

US 2017/0290894 A1 Oct. 12, 2017

Related U.S. Application Data

(60) Provisional application No. 62/321,313, filed on Apr. 12, 2016.

(51) Int. Cl.

| A61K 38/48 | (2006.01) |
|---|---|
| A61K 33/04 | (2006.01) |
| A61K 38/06 | (2006.01) |
| A61K 38/46 | (2006.01) |
| A61K 38/44 | (2006.01) |
| A61K 31/593 | (2006.01) |
| A61K 45/06 | (2006.01) |

(52) U.S. Cl.
CPC .......... *A61K 38/488* (2013.01); *A61K 31/593* (2013.01); *A61K 33/04* (2013.01); *A61K 38/063* (2013.01); *A61K 38/44* (2013.01); *A61K 38/46* (2013.01); *A61K 38/4813* (2013.01); *A61K 38/4873* (2013.01); *A61K 45/06* (2013.01); *C12Y 111/01006* (2013.01); *C12Y 304/14005* (2013.01); *C12Y 304/22032* (2013.01); *C12Y 304/22033* (2013.01); *C12Y 304/23* (2013.01)

(58) Field of Classification Search
None
See application file for complete search history.

(56) References Cited

U.S. PATENT DOCUMENTS

| 5,916,565 | A * | 6/1999 | Rose ................. A01N 65/00 424/195.1 |
| 6,204,248 | B1 * | 3/2001 | Demopoulos ........ A61K 9/0034 424/456 |
| 6,214,373 | B1 | 4/2001 | Snowden |
| 6,440,448 | B1 | 8/2002 | Intelisano |
| 6,524,625 | B2 | 2/2003 | Aga et al. |
| 6,596,298 | B2 | 7/2003 | Leung et al. |
| 7,943,312 | B2 | 5/2011 | Hausch et al. |
| 8,993,522 | B2 | 3/2015 | Vidyasagar et al. |
| 2002/0146463 | A1 | 10/2002 | Clayton |
| 2005/0260181 | A1 * | 11/2005 | Girsh ................. A61K 31/198 424/93.45 |
| 2006/0008908 | A1 * | 1/2006 | Giles ................. A61K 31/19 435/455 |
| 2006/0193928 | A1 | 8/2006 | Soman et al. |
| 2006/0257351 | A1 * | 11/2006 | Chiba ................. A61K 8/347 424/74 |
| 2008/0139525 | A1 * | 6/2008 | Loscalzo ............. A61K 31/555 514/185 |
| 2008/0193531 | A1 | 8/2008 | Hermelin et al. |
| 2008/0213401 | A1 | 9/2008 | Smith |
| 2009/0104312 | A1 | 4/2009 | Kamarei et al. |
| 2009/0220619 | A1 | 9/2009 | Cotter et al. |
| 2010/0285147 | A1 | 11/2010 | Motoune et al. |
| 2010/0291050 | A1 | 11/2010 | Daikeler et al. |
| 2013/0131007 | A1 | 5/2013 | Brown |
| 2014/0100283 | A1 * | 4/2014 | Mahoney ............. A61K 9/4866 514/562 |

OTHER PUBLICATIONS

Wentz, Using Enzymes to Overcome Hashimoto's, Webpage, Nov. 12, 2015 (Year: 2015).*
Mazokopakis, Hashimoto's thyroiditis and the role of selenium. Current concept, Hellenic Journal of Nuclear Medicine, 2007 (Year: 2007).*
Wobenzym, Douglas Laboratories, Catalog, 2017 (Year: 2017).*
DPP, AFP Peptizyde, Houston Enzymes, Catalog, Oct. 1, 2002 (Year: 2002).*
Catalase, Catalase Supplement with Picrorhiza: Catalase Hx, Webpage, Apr. 23, 2013 (Year: 2013).*
Mohen et al. (Oral Pancreatic Enzyme Therapy in the Control of Diabetes Mellitus in Tropical Calculous Pancreatitis. International Journal of Pancreatology, vol. 24. No. 1, 19-22, Aug. 1998).
Kibirige et al. (Vitamin B12 deficiency among patients with diabetes mellitus: is routine screening and supplementation justified? Journal of Diabetes & Metabolic Disorders 2013 12:17 pp. 1-6).
Dictionary.com, Organic, Available online at: www.dictionary.com/browse/organic?s=t, Accessed Jan. 29, 2018.
Bagchi et al., (Effects of Orally Administered Undernatured Type II chicken Collagen Against Arthritic Inflammatory Pathologies; A Mechanistc Exploration, International Journal of Clinical Pharmacology Research, 22(3-4):101 110 (2002)) Available at https://Citeseerx.ist.psu.edu—last viewed Jul. 5, 2018.
International Journal of Biomedical Science (Available at http://www.ijbs.org/user/ContentFullText.aspx?VolumeNo=11&StartPage=54#AB-S) Last viewed Dec. 14, 2016.
Arthritis Research and Therapy (Sasaki et al., Serum hyaluronic acid concentration predicts the progression of joint space narrowing in normal knees and established knee osteoarthritis—a five-year prospective cohort study, 17:283 (2015).

* cited by examiner

*Primary Examiner* — Louise W Humphrey
*Assistant Examiner* — Srikanth Patury
(74) *Attorney, Agent, or Firm* — FisherBroyles, LLP; Ian Walsworth

(57) ABSTRACT

The present disclosure relates to a compound and method of using such compound, preferably in the form of a dietary supplement that, when administered, is capable of treating thyroid disease and various thyroid-related disorders, such as Hashimoto's thyroiditis. The unique combination of the composition is preferably administered orally via acid resistant or enteric-coated capsule, soft gel or tablet. The composition is preferably comprised of at least Catalase, Reduced Glutathione, Acetylated Glutathione, DPP-IV protease enzyme, Pepsin, Bromelain, Pancreatin, Vitamin D, and Selenium. The composition can further comprise a palliative agent, and can be provided in specific dosages or administered in forms besides those listed above.

7 Claims, No Drawings

COMPOSITIONS AND METHODS FOR TREATING THYROID DISEASE

CROSS REFERENCE TO RELATED APPLICATIONS

This application claims priority under 35 U.S.C. § 119(e) to U.S. Provisional Application Ser. No. 62/321,313, filed Apr. 12, 2016, which is incorporated herein in its entirety by reference.

FIELD OF THE INVENTION

The present invention is directed to compounds, particularly dietary supplements, and methods for formulating and administering the same.

BACKGROUND OF THE INVENTION

The human thyroid gland is a small gland at the base of the neck below the Adam's apple. This gland, which is part of the endocrine system, naturally produces the hormones thyroxine (T4) and triiodothyronine (T3), which are essential to the proper growth, development and function of the human body. Thyroid hormones regulate the metabolism of fats, proteins and carbohydrates. In turn, the thyroid hormone affects how these compounds produce energy. In addition to these functions, thyroid hormones have several critical functions in the human body, especially pertaining to human metabolic and cardiovascular systems. For example, production of thyroid hormone supports normal body temperature, cardiac output, a healthy heart rhythm, mood, respiratory rate, basal metabolic rate (BMR) and gastric emptying.

There are presently a number of known but unresolved problems relating to the human thyroid and in general thyroid disease and thyroid-related disorders. One condition is termed "hypothyroidism" and is due to the reduced production or utilization of thyroid hormone. When the human body's own immune system targets the thyroid gland as if it were a foreign tissue, it causes an autoimmune disorder of the thyroid gland termed Hashimoto's thyroiditis; other names for this condition include chronic lymphocytic thyroiditis or chronic thyroiditis.

Hashimoto's disease is an immune disorder and condition in which the immune system attacks the thyroid. An infiltration of "lymphoid" cells and atrophy of the tissue will eventually destroy the thyroid gland. Over time, the chronic assault from the immune system and the resulting degradation of the thyroid gland causes inflammation of the glandular tissue and suppressed thyroid hormone production. In fact, Hashimoto's disease is the most common cause of hypothyroidism in the United States.

The deterioration of the thyroid gland is slow, and the thyroid hormones will fluctuate erratically at first swinging high and then low. This fluctuation can cause a person to be misdiagnosed with any number of psychiatric disorders including memory loss, brain fog, bipolar disease, anxiety, panic attacks, depression or insomnia. The condition of Hashimoto's is much more than a disease of erratic moods; these symptoms most often lead to the discovery of the condition at the clinic. When the immune system targets the thyroid gland for destruction, which it perceives it as foreign tissue, there is resulting inflammation. A long-term attack will lead to an underachieve thyroid gland (hypothyroidism). The patient goes from being euthyroid to clinically hypothyroid over a time frame that varies from months to years.

Symptoms of Hashimoto's and resulting hypothyroidism include:
  Fatigue and exhaustion
  Sensitivity to cold
  Constipation or diarrhea (digestion problems)
  Pale, dry skin or hair
  A puffy face
  Hoarse voice
  Weight gain
  Hair loss or thinning, or loss of eyebrows/lashes
  Tenderness and stiffness in the joints
  Muscle aches or weakness
  Heavy or prolonged menstrual bleeding (menorrhagia)
  Intestinal permeability
  Pain
  Depression, anxiety or mood swings
  Multiple food sensitivities (due to overactive immune function)

Hashimoto's is often detected by one of several blood tests. One of the tests measures blood levels of antibodies to an enzyme called "Thyroid Peroxidase" which is abbreviated in the medical literature as TPO. This enzyme contains a "peroxide" molecule as noted in its name "peroxidase." Finding elevated levels of TPO antibodies correlates to Hashimoto's disease and high levels of peroxide. Reducing abnormally high levels of TPO antibodies and supporting immune function is key to getting well.

Hashimoto's affects women mostly, but can occur in men or children of any age. Other problems are known to those of ordinary skill in the art. Therefore, it is desirable to provide a compound, such as a dietary supplement, that specifically addresses these immune-system problems and otherwise improves upon the healthy function of both the immune system and the human thyroid gland.

Through clinical trials, certain vitamins, minerals, enzymes or other supplements known by those in the state of the art may be useful to control or reverse the harm done by autoimmune reactions to the thyroid gland. In particular, supplements containing antioxidants, proteolytic enzymes, systemic enzymes, short chain fatty acids, and minerals may help reestablish normal immune and thyroid function in Hashimoto's sufferers. In particular, proteolytic enzymes help reduce inflammation, which is very high in people with autoimmune disorders such as Hashimoto's. Proteolytic enzymes clean the bloodstream by breaking down protein based food particles which would otherwise travel through the blood and lodge in or around the thyroid.

As blood cleansers, these proteolytic enzymes offset chronic inflammation, which if unchecked can harm the thyroid gland and spark more autoimmunity. Proteolytic enzymes are important to break down foreign proteins in the blood that cause inflammation, facilitate their removal via your lymphatic system and bloodstream, and remove "fibrin" which is a clotting material; additionally, proteolytic enzymes serve the purpose of reducing edema (swelling/inflammation) of the inflamed regions such as the thyroid gland in thyroiditis conditions.

Therefore, it would be desirable to include a proteolytic enzyme such as "protease," pancreatin or other, within a dietary supplement in order to positively influence human metabolism of thyroid hormones, and more specifically, suppress an autoimmune attack and resulting inflammatory compounds which may otherwise induce swelling and pain.

In addition to the thyroid-related problems associated with Hashimoto's, people with this condition often have severe and unrelenting food allergies due to a higher amount of intestinal permeability, which among other problems, allows immune complexes and undigested food particles to leave the tube of the gut and enter the bloodstream where immune cells perceive it as a foreign molecule (suddenly targeted to be destroyed).

The intestinal permeability makes a Hashimoto's patient more susceptible to mineral deficiencies, most notably selenium deficiency. Selenium is important to thyroid health, and thyroid hormone production. This mineral deficiency can lead to thyroid dysfunction since selenium is an essential trace mineral and a component of selenoproteins that are involved in the production of thyroid hormones and in regulating the immune response. Further, selenium deficiency is tightly correlated with elevated antibodies to the thyroid gland, namely TPO and thyroglobulin (TG) antibodies. Through experimentation it has been found that including selenium as a dietary supplement may be beneficial to people who have Hashimoto's disease.

Selenium has also been found to be beneficial to treating autoimmune thyroid disease. Recent experimentation has shown that selenium supplementation reduced TPO antibody levels in the blood, even in selenium sufficient patients. Selenium can also significantly reduce inflammatory cytokines because it is a strong mineral antioxidant.

These problems and others are addressed by the compositions and methods described in detail below.

SUMMARY OF THE INVENTION

In varying embodiments described herein, the invention relates to a compound capable of treating autoimmune thyroid disease. The unique combination of the composition is preferably administered orally, preferably in the form of a capsule. Methods for formulating the compound are also disclosed herein. The unique combination of the present invention has synergistic advantages over previously known compositions. As disclosed in more detail in the Detailed Description, the present invention provides both compositions and methods for treating autoimmune Hashimoto's thyroiditis.

The composition is preferably comprised of a unique and novel formulation in pre-determined amounts, and further provides benefits previously unexpected. In addition to other health benefits described herein, the composition provides the following benefits:

Reduces production of antibodies of TPO
Modulates the production of T4 thyroxine hormone
Reduces ammonia, a neurotoxin associated with autoimmune dysfunction
Reduces gluten and casein absorption, two food sensitivities known to trigger autoimmune reactions
Breaks down proteins in the bloodstream
Improves production of glutathione
Improves breakdown of toxic "hydrogen peroxide" turning it into healthy oxygen and water The composition of the present invention is provided by way of a non-glandular formula, which comprises supportive nutrients and enzymes for a healthy thyroid gland as well as normal and healthy immune responses.

In certain embodiments, the composition provides additional nutrients necessary for healthy thyroid and immune function.

An aspect of the invention is directed to a composition comprising at least selenium, digestive enzymes DPP-IV, proteolytic enzyme (i.e. pancreatin or bromelain), systemic enzyme (i.e. pancreatin), and antioxidants glutathione. Other ingredients can be included to promote a healthy immune response to the thyroid gland, and these are described in detail herein.

More particularly, a preferred embodiment of the present invention comprises from about 25 to 1,000 mg Catalase, from about 100 to 500 mg Reduced Glutathione, from about 10 to 200 mg of Acetylated Glutathione, from about 10 to 1,000 mg DPP-IV enzyme, from about 10 to 50 mg Pepsin, from about 50 to 500 mg Bromelain, from about 50 to 500 mg Pancreatin enzyme, and from about 25 to 200 mcg of Selenium. Some embodiments can include from about 1,000 to 10,000 IU Vitamin D.

In some embodiments, the composition can be provided as a dietary supplement in the form of a capsule that is coated to withstand stomach acid. In some embodiments, the composition can be administered in the form of an acid-resistant or enteric-coated tablet.

An aspect of the invention is a composition for treating a thyroid disorder. The composition includes selenium, a digestive enzymes DPP-IV, proteolytic enzyme, systemic enzyme, and glutathione.

An aspect of the invention is a method to manufacture a composition for treating a thyroid disease. The method includes mixing selenium, a digestive enzymes DPP-IV, proteolytic enzyme, systemic enzyme. and glutathione to form a mixture; and compressing the mixture in a capsule.

An aspect of the invention is a method to treat a patient with an autoimmune disease. The method includes providing the patient with a capsule. The capsule includes from about 25 to 200 mcg of selenium, from about 100 to 500 mg the reduced glutathione, from about 10 to 200 mg of acetylated glutathione, from about 10 to 1,000 mg DPP-IV enzyme, from about 50 to 500 mg bromelain, and from about 50 to 500 mg pancreatin enzyme.

As used herein, the phrases "at least one", "one or more", and "and/or", as used herein, are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

Unless otherwise indicated, all numbers expressing quantities, dimensions, conditions, and so forth used in the specification and claims are to be understood as being modified in all instances by the term "about".

The term "a" or "an" entity, as used herein, refers to one or more of that entity. As such, the terms "a" (or "an"), "one or more" and "at least one" can be used interchangeably herein.

The use of "including," "comprising," or "having" and variations thereof herein is meant to encompass the items listed thereafter and equivalents thereof as well as additional items. Accordingly, the terms "including," "comprising," or "having" and variations thereof can be used interchangeably herein.

It shall be understood that the term "means" as used herein shall be given its broadest possible interpretation in accordance with 35 U.S.C. Section 112(f). Accordingly, a claim incorporating the term "means" shall cover all structures, materials, or acts set forth herein, and all of the equivalents thereof. Further, the structures, materials, or acts and the equivalents thereof shall include all those described in the summary of the invention, brief description of the drawings, detailed description, abstract, and claims themselves.

These and other advantages will be apparent from the disclosure of the invention(s) contained herein. The above-described embodiments, objectives, and configurations are neither complete nor exhaustive.

The Summary of the Invention is neither intended nor should it be construed as being representative of the full extent and scope of the present invention.

Moreover, references made herein to "the present invention" or aspects thereof should be understood to mean certain embodiments of the present invention and should not necessarily be construed as limiting all embodiments to a particular description. The present invention is set forth in various levels of detail in the Summary of the Invention and the Detailed Description, and no limitation as to the scope of the present invention is intended by either the inclusion or non-inclusion of elements in this Summary of the Invention. Additional aspects of the present invention will become more readily apparent from the Detailed Description.

DETAILED DESCRIPTION

Although the following text sets forth a detailed description of numerous different embodiments, it should be understood that the legal scope of the description is defined by the words of the claims set forth at the end of this disclosure. The Detailed Description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

Composition

An aspect of the invention is directed to a composition. The composition comprises selenium, digestive enzymes DPP-IV, proteolytic enzyme, systemic enzyme, selenium, and antioxidants glutathione. Other components can be included in the composition.

Catalase

Certain individuals have a genetic mutation or a single nucleotide polymorphism (SNP—pronounced snip), which causes difficulty in converting hydrogen peroxide to its harmless byproducts. The enzyme that makes this conversion is called "catalase" and in supplemental form can break down peroxide. People with Hashimoto's have elevated levels of peroxide that must be quelled.

Catalase reduces oxidative stress by breaking down a potent free radical toxin called hydrogen peroxide which cells naturally produce each day. In patients with Hashimoto's thyroidits, there is an enormous amount of "lipid peroxidation," which is a scientific term describing the destruction (or peroxidation) of cell membranes.

Lipid preoccupation is the oxidative breakdown of lipids (fats). It is the process in which free radicals take electrons from the fats in cell membranes, resulting in cell damage. This process is proceeded by a free radical chain reaction mechanism. It spawns a lot of harmful cytokines, namely hydrogen peroxide. Catalase directly breaks down hydrogen peroxide, rendering it harmless by turning it into water and oxygen.

In some embodiments, the composition further comprises a pre-determined amount of catalase. The human body requires catalase to convert the free radical "hydrogen peroxide" into harmless water and oxygen. Without enough catalase, the body will begin to "rust" and the hair may turn grey and the build-up of peroxides will increase damage to the cells, in particular the cell membranes of the thyrocytes (thyroid cells).

People who are deficient in iron or niacin (due to drinking coffee, or taking ibuprofen or aspirin) may have insufficient levels of catalase enzyme activity. People with genetic SNPs may also be deficient in catalase.

In some embodiments, the composition can comprise from about 25 to 1,000 mg of catalase. In a preferred embodiment, the composition can comprise about 250 mg of catalase.

DPP-IV Digestive Enzyme

People with Hashimoto's have a difficult time digesting food, especially proteins. In some embodiments, the composition can include at least one digestive enzyme. The compound can include a pre-determined amount of "Dipeptidyl peptidase 4" or DPP-IV. It has been found from experimentation that DPP-IV reduces absorption of gluten and casein, two proteins found in wheat and dairy, respectively. As gluten and casein are known to attack and damage the thyroid glands of certain individuals, and set forth autoimmune attacks within the human body, it is desirable to include a pre-determined amount of DPP-IV within the composition. In addition, certain individuals have a deficiency in this enzyme, and therefore have trouble breaking down gluten and casein protein. Partial digestion of these food proteins will leak through the highly permeable intestinal lining, and travel through the bloodstream ultimately provoking an immune response. When these molecules land in or near the thyroid gland, there is an autoimmune thyroid assault.

The composition can include from about 10 to 1,000 mg of DPP-IV. In some embodiments, the composition can include about 100 mg of DPP-IV. In some embodiments, one or more additional digestive enzymes are included or substituted for DPP-IV. Suitable digestive items, for examples of DPP-IVs include, but are not limited to, amylase, cellulose, phytase, lactase, sucrose, lipase, and combinations thereof.

Pepsin

The human body forms antibodies to the various proteins which are also the same exact antibodies that could target the thyroid gland during Hashimoto's disease. When a person eats food, and the undigested food proteins and particles lodge in or around the thyroid gland, then the immune system launches an attack. These poorly digested protein/food particles become fuel for opportunistic bacteria and yeast that live in the gut microbiome. An overgrowth of these opportunistic infections leads to more gastrointestinal symptoms. Studies have shown that overgrowth of opportunistic bacteria are tied to autoimmune dysfunction of the thyroid gland. Hashimoto's symptoms increase due to the unregulated influx of pro-inflammatory (pain-causing) chemicals that leave the gut and travel throughout the bloodstream, potentially lodging in the thyroid gland.

In some embodiments, the composition further can comprise a pre-determined amount of pepsin, which can be animal or vegetable derived. Pepsin is a protein-digesting enzyme known as "proteases," whose function is to break down large proteins into their smaller particles called peptides. Pepsin has been found through experimentation to assist in the reduction of auto-antibodies aimed at the thyroid gland, so indirectly, enzymes promote a healthy thyroid function.

The composition can comprise from about 10 to 50 mg of pepsin. In some embodiments, the composition can include about 20 mg of pepsin.

Bromelain

Thyroid disorders are characterized by increased inflammation in the body and in the case of Hashimoto's thyroiditis, there is a tremendous amount of inflammation around the thyroid tissue itself. Bromelian helps reduce inflammation.

Bromelain is not a single substance, but rather a collection of protein-digesting enzymes and other compounds. It is a proteolytic enzyme that works to modulate (or coordinate) the activity of inflammatory immune complexes. Proteolytic enzymes have an affinity for immune complexes that would otherwise travel through the blood stream and increase inflammatory chemical (called cytokines) such as Tumor Necrosis Factor (TNF) and C Reactive Protein (CRP). Bromelian can reduce the reactivity of the immune complexes, which come from undigested food particles, and simultaneously reduced production of pro-inflammatory cytokines.

The composition can comprise a pre-determined amount of bromelain. The enzyme can be derived from pineapples and has been discovered through experimentation to be a desirable method of reducing inflammation. In some embodiments, the composition comprises from about 50 to 500 mg of bromelain. In some embodiments, the composition can comprise about 250 mg of bromelain.

Pancreatin

Clearly, with Hashimoto's disease, there is a need for additional support in food metabolism and breakdown. Increased intestinal permeability (commonly termed "leaky gut syndrome") is associated with autoimmune disease. In fact, reversing symptoms of autoimmune disease, including Hashimoto's depends on healing the lining of the gastrointestinal tract. Drug treatment only seeks to suppress symptoms, not heal the gut or reduce the problem of undigested food particles, which leave the gut and travel throughout the bloodstream. With Hashimoto's, the body makes antibodies to the thyroid gland. Pancreatin is a pancreatic enzyme that reduces the burden that the body has to face from partially digested food particles that leaves the "leaky gut." Pancreatin is a digestive enzyme that supports food metabolism.

The composition can include a pre-determined amount of pancreatin enzymes. Through experimentation it has been discovered that undigested food proteins which lead to thyroid autoimmunity are minimized or eliminated by pancreatin, a digestive enzyme that is naturally produced in the body by the exocrine cells of the human pancreas. Pancreatin might help to lessen the antigenic load or toxic molecules being presented on the intestinal lining and bloodstream. Pancreatin is not a single enzyme but rather it is composed of amylase, lipase and protease, which breaks down carbohydrates, fats and proteins, respectively. Studies show that supplementation of pancreatin can help with autoimmune dysfunction. Pancreatin can also be useful for flatulence, cystic fibrosis or chronic pancreatitis.

With respect to thyroid function and Hashimoto's, pancreatin may help suppress antigenic load from undigested food particles that have migrated through the leaky gut into the bloodstream and/or thyroid tissue.

The composition can include from about 50 to 500 mg of pancreatin. In some embodiments, the composition comprises about 200 mg of pancreatin enzyme.

Vitamin D

Studies show a tight correlation with vitamin D deficiency and autoimmune diseases of many sorts including Hashimoto's. Researchers in South Korea, in 2013 looked at vitamin D levels and how they correlated with the presence of the antibody TPO-Ab (antibodies to TPO, a biomarker for Hashimoto's). The presence of TPO-Ab signals that the body has or has had an attack on the thyroid.

The researchers looked at 6,685 patients between 2008 and 2012. All participants had their blood drawn, so the researchers could measure both TPO-Ab and vitamin D levels. The researchers divided patients into three different categories, those who were severely deficient in vitamin D (had levels less than 10 ng/ml), deficient in vitamin D (levels between 10-30 ng/ml) and those who were sufficient in vitamin D (over 30 ng/ml). Those who were deficient in vitamin D were much more likely to have TPO-Ab positive tests (a biomarker confirming Hashimoto's thyroiditis). The prevalence of TPO-Ab positive tests was 21.2% in the severely vitamin D deficient group, 15.5% in the deficient group, and just 12.6% in the sufficient group. Participants who lacked vitamin D more than normal, had the highest autoantibody levels against the thyroid gland. Simply put, those with the lowest levels of vitamin D had the most destruction of their thyroid gland occurring.

In a preferred embodiment, the composition further comprises a pre-determined amount of vitamin D, a natural fat-soluble antioxidant produced in the human body from ultraviolet ray (sun) exposure. Vitamin D is known to promote a healthy immune system, and is particularly useful for autoimmune conditions.

As it pertains to thyroid health and autoimmune thyroid conditions, vitamin D is the primary antioxidant to protect the thyroid gland. The composition can include from about 1,000 to 10,000 IU of vitamin D3 (cholecalciferol). In some embodiments, the composition can include about 4,000 IU vitamin D3 (cholecalciferol).

Glutathione (Reduced and Acetylated)

Glutathione is one of the human body's most powerful antioxidant and is produced naturally in the liver, and released to be used throughout the entire system. As one function, glutathione protects DNA from damage and is critical for proper mitochondrial function and energy production. If the mitochondria are damaged, you will feel more fatigue and you can't detoxify poisons from your cells. Glutathione can be taken in supplementation form.

There are a lot of benefits to taking Glutathione orally, however, taken alone in a regular form will cause it to be of little use. Glutathione rapidly degrades once it enters the stomach where the gastric (hydrochloric acid) dissolves the glutathione molecule before it can be absorbed. Acetyl Glutathione is used to help overcome the problems with absorption. Increasing the amount of Glutathione that reaches the cells, this acetylated form permeates the barriers that once held back the benefits of supplementing Glutathione orally.

The "acetylated" form can bypass stomach acid, thus improving bioavailability. S-Acetyl Glutathione can be included in the composition to ensure optimum absorption. "Reduced" glutathione is the natural form produced by the body, and can also be included in the composition.

Aside from detoxifying poison from the cell, glutathione has been shown through experimentation to break down (metabolize) hydrogen peroxide which is high in people with Hashimoto's disease. By neutralizing peroxide in the body, free radical damage is reduced.

Glutathione is a potent "heavy metal" chelator and can help clear the body of mercury, cadmium, lead and other heavy metals. People with Hashimoto's may have elevated levels of heavy metals as part of their disease, so the enhanced clearance of heavy metals is desired. Glutathione supports immune function. It also has natural antiviral activity.

A poor diet or poor intestinal permeability, as well as chronic illness will deplete human stores of glutathione and inhibit its production. The body's ability to make glutathione declines naturally with age. Individuals over the age of 45 are especially likely to be deficient. Acetyl Glutathione benefits every system in the body, and truly earns the title of our body's "Master Antioxidant" as many people refer to it.

Therefore, the composition can include from about 10 to 200 mg of S-acetylglutathoine (SAG). In some embodiments, the composition can include about 50 mg of SAG. In some embodiments, SAG can be in a reduced form. Reduced SAG can get into the blood-brain barrier.

In some embodiments, the composition can include a predetermined amount of "reduced" glutathione, which means it is in the form that is recognized and absorbed by the cells of the body. The combination of both forms of glutathione provides optimal absorption, and synergetic effects. Reduced L-glutathione is a natural compound made in the body from the amino acids glutamic acid, cysteine and glycine. Reduced glutathione is an antioxidant that protects cells and tissues by scavenging free radicals. In this process, reduced glutathione is transformed into the oxidized form. However, reduced glutathione can quickly be depleted under heavy bouts of free radical stress or exposure to compounds that require detoxification. A shift in the ratio towards the oxidized state leaves cells and tissues vulnerable to free radical damage and inflammation. The "L" designation indicates the natural molecular structure. The composition can include from about 100 to 500 mg of "reduced" glutathione. In some embodiments, the composition can include comprises about 250 mg of "reduced" glutathione.

Selenium

The composition can include a pre-determined amount of selenium. Ideally, selenium should be supplemented in a form in which it occurs naturally in foods. Although there are various forms of the mineral selenium, such as sodium selenite, which can be used for selenoprotein biosynthesis, only "Selenomethionine" is incorporated into body proteins. Selenomethionine is a natural form of selenium. Because the L-isomer of selenomethionine (termed in the literature as Se-met) is a major natural food-form of selenium, it is used in the composition, though one skilled in the art would understand that equivalent forms can be used without deviating from the invention. This form of selenium can be stored in the human and reversibly released by normal metabolic processes, thus offering an advantage over other selenium salts. Ingested selenomethionine is absorbed in the small intestine and helps with thyroid hormone production, conversion and utilization.

Selenium is a popular compound used in thyroid support formulas since it is an antioxidant mineral and is essential for the Deiodinase enzymatic system. The deiodinase enzyme converts T4 (inactive) to T3 (active) thyroid hormone. Certain selenium-dependent deiodinase enzymes therefore activate human thyroid hormone. Deficiency of selenium would result in reduced active T3 levels. Deficiency in selenium could result in clinical hypothyroidism. The composition can include from about 10 to 400 mcg of selenium. In some embodiments, the composition comprises about 100 mcg of selenium.

Other Components

In varying embodiments, the composition can be substantially free of gluten, wheat, egg, peanuts, tree nuts, dairy, sugar, corn, soy, artificial colors, preservatives, fish and shellfish, and combinations thereof.

Palatability

According to certain embodiments, the compositions described herein can further be provided with one or more palatability agents. These palatability agents serve to add flavor to the composition so that an effective dosage is easier to be ingested by a patient. It is within the scope of the present invention that any safe, flavor enhancing palatability agent can be used in a composition of the present invention. Particularly suitable palatability agents for use in the composition of the present invention include, but are not limited to, plant oils, plant hydrolysates, yeast, and yeast hydrolysates, and combinations thereof.

Method to Treat a Patient

An aspect of the invention is a method to treat a thyroid disease with a composition comprising selenium, digestive enzymes DPP-IV, proteolytic enzyme, systemic enzyme, and glutathione. The composition can include other components such as catalase, antioxidants, and pepsin, along with palatability components. The patient is treated by providing an effective amount of the composition to affect the thyroid. The capsules can be taken by the patient daily, preferably in the morning before any other food is ingested by the patient. The capsule can be acid resistant or enteric-coated capsule, soft gel or tablet. In some embodiments, the dosage can be adjusted to result in an adequate thyroid level in the patient. In some embodiments, the disease can be Hashimoto's.

Method for Making the Composition

An aspect of the invention is a method to prepare a composition. The method comprises providing proportional amounts of each component such that the resulting composition results containing from about 100 to 500 mg Reduced Glutathione, from about 10 to 200 mg of Acetylated Glutathione, from about 10 to 1,000 mg DPP-IV enzyme, from about 50 to 500 mg Bromelain, from about 50 to 500 mg Pancreatin enzyme, and from about 25 to 200 mcg of Selenium. In some embodiments, the composition can further include from about 25 to 1,000 mg Catalase, from about 10 to 50 mg Pepsin, from about 1,000 to 10,000 IU Vitamin D. The components are mixed, then can be provided to a delivery device (for example capsule or a powder). The capsule can be acid resistant or enteric-coated capsule, soft gel or tablet.

Ranges have been discussed and used within the forgoing description. One skilled in the art would understand that any sub-range within the stated range would be suitable, as would any number within the broad range, without deviating from the invention.

While various embodiment of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims. For further illustration, the book "Thyroid Healthy" authored by the named inventor of the present invention is expressly made a part of this disclosure and incorporated by reference herein in their entirety.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

What is claimed is:

1. A method to treat a patient with Hashimoto's disease, comprising administering to said patient a composition comprising:
   55 mcg of selenium;
   250 mg of reduced glutathione;
   50 mg of acetylated glutathione;
   100 mg of dipeptidyl peptidase IV (DPP-IV) enzyme;
   250 mg of bromelain;
   250 mg of catalase;
   20 mg of pepsin;
   4000 IU of vitamin D3; and
   200 mg of pancreatin enzyme.

2. The method of claim 1, wherein the composition is administered to the patient in the form of a dietary supplement.

3. The method of claim 1, wherein the composition is administered to the patient in the form of an acid resistant capsule.

4. The method of claim 1, wherein the composition is administered to the patient orally in the form of a tablet.

5. The method of claim 1, wherein the composition administered to the patient further comprises a palatability agent.

6. The method of claim 5, wherein the palatability agent is at least one of a plant oil, plant hydrolysates, yeast hydrolysates, and combinations thereof.

7. The method of claim 1, wherein the composition administered to the patient does not include gluten, wheat, egg, peanuts, tree nuts, dairy, sugar, corn, soy, fish and shellfish.

* * * * *